United States Patent [19]

Matsuda et al.

[11] Patent Number: 5,650,172
[45] Date of Patent: Jul. 22, 1997

[54] PHARMACEUTICAL PREPARATION COMPRISING FAT EMULSION OF FAT MICROPARTICLES

[75] Inventors: Saburo Matsuda, Kyoto; Shigeyuki Ishikawa, Mino; Akira Suzuki, Itami; Kenji Tsujihara, Urawa; Motoaki Ohashi, Kawaguchi, all of Japan

[73] Assignee: Tanabe Seiyaku Co., Ltd., Osaka, Japan

[21] Appl. No.: 479,143

[22] Filed: Jun. 7, 1995

Related U.S. Application Data

[63] Continuation of Ser. No. 154,434, Nov. 19, 1993, abandoned.

[30] Foreign Application Priority Data

Nov. 19, 1992 [JP] Japan ................................. 4-310621

[51] Int. Cl.⁶ ........................ A61K 9/14; A61K 9/16; A61K 9/10
[52] U.S. Cl. ........................ 424/489; 424/499; 424/502; 514/937; 514/938; 514/558; 514/561; 514/25
[58] Field of Search .................... 424/450, 489, 424/499, 502; 514/37–943, 25, 553, 558, 561

[56] References Cited

U.S. PATENT DOCUMENTS

| | | | |
|---|---|---|---|
| 4,647,586 | 3/1987 | Mizushime | 514/532 |
| 4,776,971 | 10/1988 | Nakamura | 252/312 |
| 4,816,247 | 3/1989 | Desai | 424/80 |
| 5,004,756 | 4/1991 | Ogawa | 514/655 |
| 5,098,606 | 3/1992 | Nakajima | 252/358 |
| 5,229,422 | 7/1993 | Takahashi et al. | 514/558 |
| 5,278,149 | 1/1994 | Provost | 514/23 |

FOREIGN PATENT DOCUMENTS

| | | |
|---|---|---|
| 0325244 | 7/1989 | European Pat. Off. . |
| 0331755 | 9/1989 | European Pat. Off. . |
| 0355604 | 2/1990 | European Pat. Off. . |
| 1-143834 | 6/1989 | Japan . |
| 1-249716 | 10/1989 | Japan . |

*Primary Examiner*—Gollamudi S. Kishore
*Attorney, Agent, or Firm*—Birch, Stewart, Kolasch & Birch, LLP

[57] ABSTRACT

A preparation comprising a fat emulsion of fat microparticles wherein said emulsion contains a stabilizer consisting essentially of a fatty acid, a basic amino acid and a saccharide is provided. In the preparation comprising a fat emulsion of fat microparticles of the present invention, said microparticles having a mean particle diameter of at most 100 nm are stable, and so the microparticles remain in blood without being uptaken by liver. Therefore in case of administering a pharmaceutical preparation prepared by using the above-mentioned preparation of the present invention, the pharmacological activity may be expressed at a desired site. Thus the preparation is extremely useful as a drug carrier for drug delivery system. Furthermore, the pharmaceutical preparation of the present invention which is lyophilized can be easily and rapidly reconstituted into the pharmaceutical preparation comprising a fat emulsion of stable fat microparticles having a mean particle diameter of about at most 100 nm by adding distilled water, even after a long-term storage.

7 Claims, No Drawings

PHARMACEUTICAL PREPARATION COMPRISING FAT EMULSION OF FAT MICROPARTICLES

This application is continuation of application Ser. No. 08/154,434 filed on Nov. 19, 1993, now abandoned.

BACKGROUND OF THE INVENTION

The present invention relates to a pharmaceutical preparation comprising a fat emulsion of fat microparticles.

In recent years there have been attempted to use, as a drug carrier for a fat-soluble medicinal compound, fat particles in fat emulsion which has been therapeutically employed as a neutritional support for patients after an operation. In conventional fat emulsion for supplying nutrition, however, even relatively small fat particles have a mean particle diameter of as large as 200 nm have been used. When fat particles having such a large particle diameter are used for a pharmaceutical preparation comprising fat particles containing a medicinal compound, the pharmaceutical preparation is, when administered, mostly uptaken by reticuloendothelial system such as liver and spleen, and therefore, the medicinal compound cannot be delivered to a desired site. So, it has been attempted to use fat microparticles so that they may not be uptaken by reticuloendothelial system and the medicinal compound may be delivered to the desired site. As such pharmaceutical preparation comprising a fat emulsion of fat microparticles, there have been known, for example, a fat emulsion of fat microparticles having a mean particle diameter of 40 nm to 70 nm which contain a benzo[a]phenazine anticancer drug (Japanese Unexamined Patent Publication No. 143834/1989) and a fat emulsion of fat microparticles having a mean particle diameter of 10 nm to 40 nm which contain a fat-soluble medicinal compound (Japanese Unexamined Patent Publication No. 249716/1989).

However, in a system containing microparticles, their particle diameter tends to increase with a lapse of time owing to the flocculation or coalescence thereof. Therefore, it has been difficult to obtain a long-term stable pharmaceutical preparation comprising a fat emulsion of fat microparticles.

From the viewpoint of handling, transportation and storage in a practical use of a pharmaceutical preparation, a pharmaceutical preparation comprising a fat emulsion of fat microparticles which can be stored usually as the lyophilized pharmaceutical preparation and can be easily reconstituted into the pharmaceutical preparation comprising a fat emulsion of stable fat microparticles by adding a solvent such as distilled water for injection before using, will be extremely advantageous. However, it has been very difficult to obtain such a pharmaceutical preparation.

An object of the invention is to provide a pharmaceutical preparation comprising a fat emulsion of fat micropaticles, which can be usually stored for a long period as a lyophilized product and can be easily reconstituted into the pharmaceutical preparation comprising a fat emulsion of stable fat microparticles by adding a solvent such as water, by which pharmaceutical preparation, a medicinal compound can be retained in the blood without being uptaken by the reticuloendothelial system.

This and other objects of the present invention will become apparent from the description hereinafter.

SUMMARY OF THE INVENTION

It has been found that a pharmaceutical preparation comprising a fat emulsion of fat microparticles, which is prepared by using a stabilizer consisting essentially of a fatty acid, a basic amino acid and a saccharide, is stable for a long term, and that a lyophilized product thereof can be easily reconstituted into the pharmaceutical preparation comprising a fat emulsion of fat microparticles by adding an aqueous solvent such as water or saline and shaking before using.

In accordance with the present invention, there is provided a preparation as a drug carrier comprising a fat emulsion of fat microparticles, wherein said emulsion contains a stabilizer consisting essentially of a fatty acid, a basic amino acid and a saccharide.

According to the present invention, there is also provided a pharmaceutical preparation comprising a fat emulsion of fat microparticles containing a fat-soluble medicinal compound wherein said emulsion contains a stabilizer consisting essentially of a fatty acid, a basic amino acid and saccharide.

Because in the pharmaceutical preparation of the present invention, fat microparticles having a mean particle diameter of at most 100 nm are stable, the microparticles remain in the blood without being uptaken by the liver. Therefore, in case of administering a pharmaceutical preparation of the present invention, the pharmacological activity may be revealed at the desired site. Thus the preparation of the present invention is extremely useful as a drug carrier for a drug delivery system. Furthermore, the pharmaceutical preparation of the present invention which is lyophilized (hereinafter referred to as "lyophilized pharmaceutical preparation") can be easily and rapidly reconstituted into the pharmaceutical preparation comprising a fat emulsion of stable fat microparticles having a mean particle diameter of about at most 100 nm by adding an aqueous solvent such as distilled water or saline, even after a long-term storage.

DETAILED DESCRIPTION

A fat which forms microparticles is not particularly limited in the present invention, and there can be used any fat which is liquid at ordinary temperature and is administerable per tubam. Fats and oils generally used for fat emulsion are preferable.

Representative examples of the above-mentioned fat and oil are, for instance, a vegetable oil such as purified soybean oil, corn oil, rapeseed oil, peanut oil or safflower oil; a fish oil; a synthetic fat and oil such as a triglyceride of medium chain fatty acid having 8 to 10 carbon atoms (Panasate 800, Panasate 810 and Panasate 875, all of them trade names, commercially available from Nippon (Oil & Fats Co., Ltd.), squalene or AZONE (trademark), of which the chemical name is 1-dodecylazacycloheptan-2-one, commercially available from Nelson Research USA), and the like. Among these examples, purified soybean oil and a triglyceride of medium chain fatty acid are preferable.

These fats can be used alone or in an admixture thereof.

The above-mentioned fat is suitably contained in an amount of about 1 to about 50 w/v %, preferably about 5 to about 20 w/v %, in the preparation comprising a fat emulsion of fat microparticles of the present invention.

As a fatty acid which is used as one component of a stabilizer in the present invention, there can be exemplified a saturated or unsaturated fatty acid having 6 to 32 carbon atoms.

Representative examples of the above-mentioned fatty acid include caproic acid, enanthic acid, caprylic acid, pelargonic acid, capric acid, undecylic acid, lauric acid, tridecylic acid, myristic acid, pentadecylic acid, palmitic acid, heptadecylic acid, stearic acid, oleic acid, nonadecanoic acid, arachic acid, linoleic acid, linolenic acid, behenic acid, lignoceric acid, cerotic acid, heptacosanoic acid, montanic acid, melissic acid, lacceric acid, elaidic acid and brassidic acid.

Among these, fatty acids having about 6 to about 21 carbon atoms such as caproic acid, enanthic acid, caprylic acid, pelargonic acid, capric acid, undecylic acid, lauric acid, tridecylic acid, myristic acid, pentadecylic acid, palmitic acid, heptadecylic acid, stearic acid, oleic acid, nonadecanoic acid, arachic acid, linoleic acid, linolenic acid and behenic acid are preferable. Further, fatty acids such as oleic acid, linoleic acid, myristic acid, stearic acid, palmitic acid and behenic acid are more preferable.

These fatty acids can be used alone or suitably in an admixture thereof.

The above-mentioned fatty acid is suitably contained in an amount of about 0.01 to about 2 w/v %, preferably about 0.5 to about 1 w/v %, in the preparation comprising a fat emulsion of fat microparticles of the present invention.

As a basic amino acid which is used together with the above-mentioned fatty acid for stabilizing fat microparticles, there can be exemplified lysine, histidine, ornithine, arginine and the like.

Among these, lysine and ornithine, particularly lysine are preferable.

It is preferable that these basic amino acids have a purity usable for injection and are in a free form.

These basic amino acids can be used alone or suitably in an admixture thereof.

The above-mentioned basic amino acid is suitably contained in an amount of about 0.05 to about 1 w/v %, preferably about 0.2 to about 0.8 w/v % so as to be equimolar with the above-mentioned fatty acid, in the preparation comprising a fat emulsion of fat microparticles of the present invention.

As a saccharide which is also used for a stabilizer together with the above-mentioned fatty acid and the basic amino acid, a monosaccharide or a disaccharide wherein two monosaccharide molecules are linked, are preferable.

Representative examples of the above-mentioned saccharide include glucose, fructose, maltose, lactose, sucrose, trehalose and the like. Among these, maltose, trehalose and sucrose are preferable.

These saccharides can be also used alone or suitably in an admixture thereof.

The above-mentioned saccharide is suitably contained in an amount of about 2 to about 30 w/v %, preferably about 5 to about 20 w/v % in the preparation comprising a fat emulsion of fat microparticles of the present invention.

As to the proportions of the components of the stabilizer, namely a fatty acid, a basic amino acid and a saccharide in the preparation of the present invention, there may be used, for example, about 0. 0 5 to about 4 parts by weight of the basic amino acid and about 2 to about 80 parts by weight of the saccharide, preferably, about 0.1 to about 2 parts by weight of the basic amino acid and about 4 to about 60 parts by weight of the saccharide, more preferably, about 0.4 to about 1.6 parts by weight of the basic amino acid and about 10 to about 40 parts by weight of the saccharide, per part by weight of the fatty acid.

In the pharmaceutical preparation comprising a fat emulsion of fat microparticles of the present invention which further comprises a fat-soluble medicinal compound, any fat-soluble medicinal compound can be suitably used without particular limitation. For example, on the basis of distribution coefficient between water and octanol, a compound having a large distribution coefficient e.g. at least 2, is preferable. Further, a compound having a distribution coefficient of about 2 to abut 6, particularly abut 4 to about 6 is more preferable.

Representative examples of the above-mentioned medicinal compound are, for example, an antiinflammatory drug, a platelet aggregation inhibiting agent, a fibrinolysis-promoting agent, an antitumour agent, a fat-soluble vitamin and the like.

As concrete antiinflammatory drugs, there can be exemplified steroidal antiinflammatory drugs such as a fatty acid ester of paramethasone, nonsteroidal antiinflammatory drugs such as indomethacin and a derivative thereof, and the like. As concrete antitumour agents, there can be exemplified fluorouridine derivatives such as 3',5'-O-di-n-butanoyl-3-n-heptanoyloxymethyl-2'-deoxy-5-fluorouridine, 3',5'-O-di-n-butoxycarbonyl-3-n-heptanoyloxymethyl-2'-deoxy-5-fluorouridine, 3',5'-O-di-i-butoxycarbonyl-3-n-heptanoyloxymethyl-2'-deoxy-5-fluorouridine, 3',5'-O-dipropionyl-3-n-octanoyloxymethyl-2'-deoxy-5-fluorouridine and 3',5'-O-di-n-octanoyl-3-n-butanoyloxymethyl-2'-deoxy-5-fluorouridine, and the like. As concrete fat-soluble vitamins, there can be exemplified tocopherol acetate and the like.

The above-mentioned medicinal compound may be suitably used within a range of amount which can express its drug efficacy, according to disease to be treated and condition, age, body weight and nature of a patient to be treated. For example, in case that an antitumour agent such as a fluorouridine derivative is used as a medicinal compound, the compound may be used in an amount of about 0.01 to about 12 w/v %, preferably about 0.1 to about 6 w/v %, more preferably about 0.3 to about 4 w/v % in the pharmaceutical preparation comprising a fat emulsion of fat microparticles of the present invention.

The lyophilized pharmaceutical preparation can be obtained by lyophilizing the pharmaceutical preparation comprising a fat emulsion of fat microparticles which contains a fat-soluble medicinal compound. In the lyophilized pharmaceutical preparation of the present invention, there preferably remains about 0.1 to about 5% W/W of water. Both forms of the pharmaceutical preparation of the present invention, namely, emulsion and lyophilized product thereof can be prepared according to a conventionally known process.

The process for preparing the pharmaceutical preparation of the present invention is concretely explained below.

For example, a fatty acid and, if necessary, a fat-soluble medicinal compound are added to a fat and the mixture is dissolved at room temperature or with heating. The obtained solution is added to an aqueous solvent (e.g., distilled water, silane) containing an emulsifier, a basic amino acid, a saccharide and, if necessary, a suitable auxiliary substance, followed by mixing. The obtained mixture is crudely homogenized to give a crude emulsion containing fat particles having a mean particle diameter of about 1 μm. The obtained crude emulsion was adjusted to a desired pH with an organic acid such as malic acid and then finely emulsified to give a fine emulsion containing fat microparticles having a mean particle diameter of at most 100 nm.

Alternatively, a dispersion of an emulsifier is added to a solution which is prepared by adding a fatty acid and, if necessary, a fat-soluble medicinal compound to a fat and then dissolving the obtained mixture at room temperature or with heating. The obtained mixture is crudely homogenized and then, a basic amino acid is added thereto. The pH of the obtained mixture is adjusted with an organic acid such as malic acid and the concentration thereof is suitably adjusted by adding an aqueous solvent such as distilled water for injection. After the obtained crude emulsion is further finely emulsified, a saccharide is added thereto and the concentration is adjusted to give a fine emulsion containing fat microparticles having a mean particle diameter of at most 100 nm.

The crude-homogenation can be easily carried out by using, for example, a homogenizer at room temperature or with heating. The fine-emulsification can be carried out by using, for example, a high energy homogenizer such as Gaulin type homogenizer or Nanomizer System (trade name, made by Nanomizer Inc., Japan).

On the emulsification, an emulsifier may be advantageously used as mentioned above. The emulsifier to be used is not particularly limited and there can be used any emulsifier generally usable in this technical field.

Representative examples of such emulsifier include a lecithin such as yolk lecithin or soybean lecithin, a natural phosphatide derived from an animal such as cattle or pig, a semi-synthetic phosphatide such as phosphatidylcholine, phosphatidylethanolamine, phosphatidylserine, phosphatidylinositol, phosphatidyl-glycerol or a hydrogenated compound thereof, and the like.

These emulsifiers may be used alone or in an admixture thereof.

The above-mentioned emulsifier is suitably contained in an amount of about 0.5 to about 20 w/v %, preferably about 1 to about 10 w/v % on the basis of total volume of the preparation comprising a fat emulsion of fat microparticles of the present invention.

Further, additives or auxiliary substances such as an antioxidant, an antiseptic, an isotonic agent and a buffering agent, which are pharmaceutically acceptable and generally usable in this technical field, may be used in a suitable amount.

A lyophilized pharmaceutical preparation of the present invention can be prepared by further lyophilizing thus obtained pharmaceutical preparation comprising a fat emulsion of fat microparticles according to a known conventional method.

For example, after mechanically sterilizing thus obtained pharmaceutical preparation comprising a fat emulsion of fat microparticles, a prescribed amount thereof is poured into a vessel for lyophilization and then pre-frozen at about $-40°$ to about $-25°$ C. for about 10 hours. Then, the first primary drying is carried out under reduced pressure at about $0°$ to about $10°$ C. for about 30 hours and successively the secondary drying is carried out under reduced pressure at about $15°$ to about $25°$ C. for about 10 hours, to give the lyophilized pharmaceutical preparation of the present invention.

The present invention is more specifically described and explained by means of the following Examples. It is to be understood that the present invention is not limited to the Examples, and various changes and modifications may be made in the invention without departing from the spirit and scope thereof.

EXPERIMENTAL EXAMPLE (1) Preparation of Pharmaceutical Preparation

Pharmaceutical Preparation 1 (Pharmaceutical Preparation of the Present Invention)

There were sufficiently mixed 100 g of soybean oil and 5 g of oleic acid, and thereto was added 4 g of paramethasone palmitate as a fat-soluble medicinal compound. The obtained mixture was heated to about 40° C. and dissolved. Thereto was added a dispersion prepared by dispersing 48 g of yolk lecithine into 450 ml of previously deoxidized distilled water, followed by mixing. By using a homogenizer (Ultra-turrax, trade name, made by Ika WERK, Germany), the obtained mixture was mixed with stirring at about 10000 rpm for about 10 minutes to give a crude emulsion. To thus obtained crude emulsion was added 2.6 g of L-lysine and the mixture was adjusted to pH 7.5 with malic acid. Thereto was added a suitable amount of distilled water for injection to make the total volume of 900 ml. After the obtained crude emulsion was allowed to stand under reduced pressure for about 10 to about 20 minutes for deaeration, it was finely emulsified under high pressure at 40° C., emulsifying a pressure of 1000 $kgf/cm^2$ by means of a high energy homogenizer (Nanomizer System LA-11, trade name made, by Nanomizer Inc., Japan) to give a fine emulsion. Then 100 g of maltose was added to the obtained fine emulsion, and dissolved therein. The total volume thereof was made to 1000 ml to give a pharmaceutical preparation comprising a fat emulsion of fat microparticles.

Every about 3 ml of the obtained pharmaceutical preparation was put into a 10 ml-glass vial, and pre-frozen by means of a lyophilizing machine (Minifast 1700, trade name, made by Edwards, Great Britain) at −25° C. for 6 hours. The pre-frozen pharmaceutical preparation was primarily dried under reduced pressure at 0° C. for 30 hours, and further secondly dried under reduced pressure at 20° C. for 8 hours to give a lyophilized pharmaceutical preparation (hereinafter, referred to as "Pharmaceutical preparation 1").

Control Pharmaceutical Preparation 1

In the same manner as described in the above-mentioned Pharmaceutical preparation 1 except that oleic acid and maltose were not used, there was prepared a lyophilized pharmaceutical preparation (hereinafter, referred to as "Control pharmaceutical preparation 1").

Control Pharmaceutical Preparation 2

In the same manner as described in the above-mentioned Pharmaceutical preparation 1 except that oleic acid was not used, there was prepared a lyophilized pharmaceutical preparer ion (hereinafter, referred to as "Control Pharmaceutical Preparation 2").

(2) Storage Stability Test

With respect to (i) each pharmaceutical preparation in the form of emulsion just after the fine-emulsification, (ii) each lyophilized pharmaceutical preparation thereof just after the lyophilization and (iii) each lyophilized pharmaceutical preparation after storage at 40° C. for 1 month, a mean particle diameter of fat microparticles was measured in order to examine their stability.

In the above-mentioned measurement, both lyophilized pharmaceutical preparations just after the lyophilization and after the storage for 1 month were reconstituted into an emulsion for the measurement by adding 3 ml of distilled water for injection respectively and lightly shaking.

The mean particle diameter was measured by means of a light-scattering photometer (quasi-elastic laser light scattering particle sizer) (ELS-800 type, trade name, made by OTSUKA ELECTRONICS, Japan).

(3) Results

The results are shown in Table 1. In the pharmaceutical preparations of the present invention, the fat microparticles had a mean particle diameter of at most 100 nm and were stable at any stage, namely, just after the fine-emulsification, just after the lyophilization and after the storage with heating. On the contrary, in the control pharmaceutical preparations, not only there could not be obtained microparticles having a mean particle diameter of at most 100 nm in spite of fine-emulsification, but also it is shown that during the lyophilization or the storage, the mean particle diameter of the fat particles was further enlarged or the particles were destroyed.

trade name, available from Nippon Oil Fats Co., Ltd., Japan), 5 g of oleic acid, 48 g of yolk lecithin, 2.6 g of L-lysine, 4 g of paramethasone palmitate and 100 g of maltose, there was prepared a pharmaceutical preparation comprising a fat emulsion of fat microparticles having a mean particle diameter of about 70 nm.

The obtained pharmaceutical preparation was pre-frozen at −25° C. for 10 hours, and lyophilized at 0° C. for 40 hours, and further at 20° C. for 8 hours to give a lyophilized pharmaceutical preparation containing fat microparticles.

TABLE I

| | | Mean particle diameter of fat particles (nm) | | |
|---|---|---|---|---|
| | Component of Stabilizer | Just after fine-emulsification | Just after lyophilization | After storage at 40° C. for 1 month |
| Present invention | | | | |
| Pharmaceutical preparation 1 | Oleic acid L-Lysine Maltose | 88 | 94 | 98 |
| Control | | | | |
| Control pharmaceutical preparation 1 | L-Lysine | 141 | Unmeasurable because of viscous oily state of the pharmaceutical preparation | Unmeasurable because of viscous oily state of the pharmaceutical preparation |
| Control pharmaceutical preparation 2 | L-Lysine Maltose | 145 | 160 | 190 |

EXAMPLE 1

There were sufficiently mixed 100 g of soybean oil and 5 g of oleic acid, and thereto was added 1 g of free diltiazem as a fat-soluble medicinal compound. The obtained mixture was heated to about 40° C. and dissolved. Thereto was added a dispersion prepared by dispersing 48 g of yolk lecithine into 450 ml of previously deoxidized distilled water, followed by mixing. By using a homogenizer (Utra-turrax), the obtained mixture was mixed with stirring at about 10000 rpm for about 10 minutes to give a crude emulsion. To thus obtained crude emulsion was added 2.6 g of L-lysine and the mixture was adjusted to pH 7.5 with malic acid. Thereto was added a suitable amount of distilled water for injection to make the total volume of 900 ml. After the obtained crude emulsion was allowed to stand under reduced pressure for about 10 to about 20 minutes for deaeration, it was finely emulsified under high pressure (1000 kgf/cm$^2$) at 40° C., by means of a high energy homogenizer (Nanomizer System LA-11, trade name) to give a fine emulsion. Then 100 g of trehalose was added to the obtained fine emulsion, and dissolved therein. The total volume thereof was made to 1000 ml to give a pharmaceutical preparation comprising a fat emulsion of fat microparticles.

The obtained pharmaceutical preparation was pre-frozen at −25° C. for 6 hours, and lyophilized at 0° C. for 30 hours, and further at 20° C. for 8 hours to give a lyophilized pharmaceutical preparation comprising a fat emulsion of fat microparticles of the present invention.

When the lyophilized pharmaceutical preparation was reconstituted into a fat emulsion by adding distilled water, the mean particle diameter of fat microparticles therein was found to be about 90 nm, which was not different from that in the pharmaceutical preparation before the lyophilization.

EXAMPLE 2

In the same manner as described in Example 1 except for using 100 g of triglyceride of capric acid (Panasate 800, When the lyophilized pharmaceutical preparation was reconstituted into a fat emulsion by adding distilled water, the mean particle diameter of fat microparticles therein was found to be about 70 nm, which was not different from that in the pharmaceutical preparation before the lyophilization.

EXAMPLE 3

In the same manner as described in Example 1 except for using 100 g of soybean oil, 5 of oleic acid, 48 g of yolk lecithine, 2.6 g of L-lysine, 20 g of tocopherol acetate as a fat-soluble medicinal compound and 100 g of trehalose, there was prepared a pharmaceutical preparation comprising a fat emulsion of fat microparticles having a mean particle diameter of about 100 nm.

The obtained pharmaceutical preparation was pre-frozen at −25° C. for 6 hours, and lyophilized at 0° C. for 30 hours and further at 20° C. for 8 hours to give a lyophilized ed pharmaceutical preparation containing fat microparticles.

When the lyophilized pharmaceutical preparation was reconstituted into a fat emulsion by adding distilled water, the mean particle diameter of fat microparticles therein was found to be about 100 nm, which was not different from that in the pharmaceutical preparation before the lyophilization.

EXAMPLE 4

In the same manner as described in Example 1 except for using 100 g of Panasate 800, 5 g of oleic acid, 48 g of yolk lecithin, 2.6 g of L-lysine, 20 g of 3',5'-O-di-n-butanoyl-3-n-heptanoyloxymethyl-2'-deoxy-5-fluorouridine and 100 g of maltose, there was prepared a pharmaceutical preparation comprising a fat emulsion of fat microparticles having a mean particle diameter of about 90 nm.

The obtained pharmaceutical preparation was pre-frozen at −25° C. for 10 hours, and lyophilized at 0° C. for 40 hours and further at 20° C. for 8 hours to give a lyophilized pharmaceutical preparation comprising a fat emulsion of fat microparticles of the present invention.

When the lyophilized pharmaceutical preparation was reconstituted into a fat emulsion by adding distilled water, the mean particle diameter of fat microparticles therein was found to be about 90 nm, which was not different from that in the pharmaceutical preparation before the lyophilization.

EXAMPLES 5 TO 8

In the same manner as described in Example 4 except for using each of the following medicinal compounds as a fat-soluble medicinal compound, there were prepared lyophilized pharmaceutical preparations comprising a fat emulsion of fat microparticles containing each of them.

Medicinal compound:

3',5'-O-di-n-butoxycarbonyl-3-n-heptanoyloxy-methyl-2'-deoxy-5-fluorouridine

3',5'-O-di-i-butoxycarbonyl-3-n-heptanoyloxy-methyl-2'-deoxy-5-fluorouridine

3',5'-O-dipropionyl-3-n-octanoyloxymethyl-2'-deoxy-5-fluorouridine

3',5'-O-di-n-octanoyl-3-n-butanoyloxymethyl-2'-deoxy-5-fluorouridine

EXAMPLE 9

In the same manner as described in Example 1 except for using 100 g of a triglyceride of fatty acid (Panasate 810, trade name, composition of the fatty acid: caprylic acid/capric acid=85/15, available from Nippon Oil & Fats Co., Ltd.), 5 g of linoleic acid, 48 g of yolk lecithin, 2.6 g of L-lysine, 20 g of 3',5'-O-di-n-butanoyl-3-n-heptanoyloxymethyl-2'-deoxy-5-fluorouridine and 10 g of sucrose, there was prepared a pharmaceutical preparation comprising a fat emulsion of fat microparticles having a mean particle diameter of about 85 nm.

The obtained pharmaceutical preparation was pre-frozen at −30° C. for 8 hours, and lyophilized at 5° C. for 36 hours and further at 25° C. for 8 hours to give a lyophilized pharmaceutical preparation comprising a fat emulsion of fat microparticles of the present invention.

When the lyophilized pharmaceutical preparation was reconstituted into a fat emulsion by adding distilled water, the mean particle diameter of fat microparticles therein was found to be about 90 nm, which was not different from that in the pharmaceutical preparation before the lyophilization.

EXAMPLE 10

In the same manner as described in Example 1 except for using 100 g of a triglyceride of fatty acid (Panasate 875, trade name, composition of the fatty acid: caprylic acid/capric acid=75/25, available from Nippon Oil & Fats Co., Ltd.), 5 g of oleic acid, 48 g of yolk lecithin, 2.4 g of L-ornithine, 5 g of tocopherol acetate and 10 g of maltose, there was prepared a pharmaceutical preparation comprising a fat emulsion of fat microparticles having a mean particle diameter of about 80 nm.

EXAMPLE 11

In the same manner as described in Example 1 except for using 100 g of Panasate 800, 5 g of linoleic acid, 48 g of yolk lecithin, 2.4 g of L-ornithine, 20 g of 3',5'-O-di-n-butanoyl-3-n-heptanoyloxymethyl-2'-deoxy-5-fluorouridine and 10 of trehalose, there was prepared a pharmaceutical preparation comprising a fat emulsion of fat microparticles having a mean particle diameter of about 90 nm.

EXAMPLE 12

In the same manner as described in Example 1 except for using 100 g of soybean oil, 5 g of stearic acid, 48 g of yolk lecithin, 2.6 g of L-lysine, 20 g of 3',5'-O-di-n-butoxycarbonyl-3-n-heptanoyloxymethyl-2'-deoxy-5-fluorouridine and 10 g of maltose, there was prepared a pharmaceutical preparation comprising a fat emulsion of fat microparticles having a mean particle diameter of about 90 nm.

EXAMPLE 13

In the same manner as described in Example 1 except for using 100 g of Panasate 800, 5 g of myristic acid, 48 g of yolk lecithin, 2.1 g of L-lysine, 20 g of 3',5'-O-dipropionyl-3-n-octanoyloxymethyl-2'-deoxy-5-fluorouridine and 10 g of maltose, there was prepared a pharmaceutical preparation comprising a fat emulsion of fat microparticles having a mean particle diameter of about 80 nm.

REFERENCE EXAMPLE 1

(a) To 70 ml of acetone was added 4.95 g of 5-fluoro-2'-deoxyuridine and 12 g of sodium iodide. With stirring at room temperature, thereto was added 7.19 g of chloromethyl n-heptanoate and 15 g of anhydrous potassium carbonate. After the mixture was reacted with stirring at room temperature overnight, the obtained mixture was concentrated under reduced pressure. To the concentrate was added 150 ml of ethyl acetate, and then the insoluble matter was separated by filtration. The flitrate was washed with water, saturated aqueous solution of sodium chloride and water successively, followed by concentrating. The obtained concentrate was purified by silica gel column chromatography (eluting solvent: ethyl acetate) to give 4.77 g of 3-n-heptanoyloxymethyl-2'-deoxy-5-fluorouridine in the form of colorless solid matter (yield: 61.1%). The melting point of the obtained solid matter was 104° to 106° C.

(b) Into 30 ml of methylene chloride was dissolved 583 mg of the colorless solid matter obtained in the above (a). With stirring under cooling with ice, thereto was added 1.05 ml of triethylamine and then dropwise a methylene chloride solution containing 480 mg of butanoyl chloride.

After the mixture was reacted at room temperature for 2 hours, the obtained solution was washed with cold water, cold aqueous solution of sodium bicarbonate and saturated aqueous solution of sodium chloride successively. After the solvent was distilled away, the obtained residue was purified by silica gel column chromatography (eluting solvent: ethyl acetate/n-hexane=¼) to give 760 mg of 3',5'-O-di-n-butanoyl-3-n-heptanoyloxymethyl-2'-deoxy-5-fluorouridine in the form of colorless oily mater (yield: 89.0%). The solubility of the obtained oily matter in soybean oil was more than 300 mg/ml.

IR (Neat): $v_{max}$ (cm$^{-1}$) 1740, 1690, 1680, 1470, 1280, 1170, 1100

REFERENCE EXAMPLE 2

In the same manner as described in Reference Example 1(b) except for using 2.25 g of the product obtained in Reference Example 1(a) and 1.74 g of n-butyl chloroformate, there was prepared 2.63 g of 3',5'-O-di-n-butoxycarbonyl-3-n-heptanoyloxymethyl-2'-deoxy-5-fluorouridine in the form of colorless oily matter (yield: 77.2%).

IR (Neat): $v_{max}$ (cm$^{-1}$) 1750, 1690, 1680, 1470, 1260

REFERENCE EXAMPLE 3

In the same manner as described in Reference Example 1(b) except for using 1.5 0 g of the product obtained in Reference Example 1(a), 1.19 g of i-butyl chloroformate and 30 ml of pyridine, there was prepared 2.63 g of 3',5'-O-di-i-butoxycarbonyl-3-n-heptanoyloxy-methyl-2'-deoxy-5-fluorouridine in the form of pale yellow oily matter (yield: 86.5%).

IR (Neat): $v_{max}$ (cm$^{-1}$) 3095, 2960, 2875, 1748, 1695, 1680

REFERENCE EXAMPLE 4

(a) In the same manner as described in Reference Example 1(a) except for using 3 g of 5-fluoro-2'-deoxyuridine, 9.10 g of anhydrous potassium carbonate, 6.58 g of sodium iodide and 4.70 g of chloromethyl n-octanoate, there was prepared 3.17 g of 3-n-octanoyloxymethyl-2'-deoxy-5-fluorouridine in the form of colorless crystal (yield: 64.7%). The melting point of the obtained crystal was 74.0° to 77.9° C.

(b) In the same manner as described in Reference Example 1(b) except for using 1.50 g of the product obtained in the above (a), 1.03 g of propionyl chloride and 30 ml of pyridine, there was prepared 1.07 g of 3',5'-O-dipropionyl-3-n-octanoyloxymethyl-2'-deoxy-5-fluorouridine in the form of pale yellow oily matter (yield: 55.8%).

IR (Neat): $v_{max}$ (cm$^{-1}$) 1740, 1680

REFERENCE EXAMPLE 5

(a) In the same manner as described in Reference Example 1(a) except for using 2.2 g of 5-fluoro-2'-deoxyuridine, 6.67 g of anhydrous potassium carbonate, 4.82 g of sodium iodide and 2.44 g of chloromethyl n-butanoate, there was prepared 1.82 g of 3-n-butanoyloxymethyl-2'-deoxy-5-fluorouridine in the form of white powder (yield: 58.9%). The melting point of the obtained powder was 103.0° to 105.0° C.

(b) In the same manner as described in Reference Example 1(b) except for using 1.50 g of the product obtained in the above (a), 1.76 g of n-octanoyl chloride and 20 ml of pyridine, there was prepared 1.16 g of 3',5-O'di-n-octanoyl-3-n-butanoyloxymethyl-2'-deoxy-5-fluorouridine in the form of pale yellow oily matter.

IR (Neat): $v_{max}$ (cm$^{-1}$) 1740, 1681

In addition to the ingredients used in the Examples, other ingredients can be used in the Examples as set forth in the specification to obtain substantially the same results.

What is claimed is:

1. A lyophilized preparation which is obtainable by lyophilizing a fat emulsion of microparticles having a mean particle diameter of at most 100 nm useful as a drug carrier, said fat emulsion comprising (a) said microparticles of a fat or oil in an amount of 1 to 50 w/v %, (b) a fatty acid in an amount of 0.01 to 2 w/v %, (c) a basic amino acid in an amount of 0.05 to 1 w/v %, and (d) a saccharide in an amount of 2 to 30 w/v %;

wherein the fat or oil is at least one member selected from the group consisting of a vegetable oil, a fish oil, a triglyceride of a medium chain fatty acid, squalene and 1-dodecylazacycloheptan-2-one; the fatty acid is a fatty acid having 6 to 32 carbon atoms; the saccharide is at least one member selected from the group consisting of glucose, fructose, maltose, lactose, sucrose and trehalose; and the basic amino acid is at least one member selected from the group consisting of lysine, histidine, ornithine and arginine.

2. A lyophilized pharmaceutical preparation which is obtainable by lyophilizing a fat emulsion of microparticles having a mean particle diameter of at most 100 nm comprising (a) said microparticles of a fat or oil in an amount of 1 to 50 w/v % containing a fat-soluble medicinal compound, (b) a fatty acid in an amount of 0.01 to 2 w/v %, (c) a basic amino acid in an amount of 0.05 to 1 w/v %, and (d) a saccharide in an amount of 2 to 30 w/v %;

wherein the fat or oil is at least one member selected from the group consisting of a vegetable oil, a fish oil, a triglyceride of a medium chain fatty acid, squalene and 1-dodecylazacycloheptan-2-one; the fatty acid is a fatty acid having 6 to 32 carbon atoms; the saccharide is at least one member selected from the group consisting of glucose, fructose, maltose, lactose, sucrose and trehalose; and the basic amino acid is at least one member selected from the group consisting of lysine, histidine, ornithine and arginine.

3. The lyophilized preparation of claim 1 or 2, wherein the fatty acid is at least one member selected from the group consisting of oleic acid, linoleic acid, myristic acid, stearic acid, palmitic acid and behenic acid.

4. The preparation of claim 2, wherein the fat-soluble medicinal compound is at least one member selected from the group consisting of 3',5'-O-di-n-butanoyl-3-n-heptanoyloxymethyl-2'-deoxy-5-fluorouridine, 3',5'-O-di-n-butoxycarbonyl-3-n-heptanoyloxymethyl-2'-deoxy-5-fluorouridine, 3',5'-O-di-i-butoxycarbonyl-3-n-heptanoyloxymethyl-2'-deoxy-5-fluorouridine, 3',5'-O-dipropionyl-3-n-octanoyloxymethyl-2'-deoxy-5-fluorouridine, 3',5'-O-di-n-octanoyl-3-n-butanoyloxymethyl-2'-deoxy-5-fluorouridine and a fatty acid ester of paramethasone.

5. The preparation of claim 1 or 2, wherein 0.05 to 4 parts by weight of the basic amino acid, and 2 to 80 parts by weight of the saccharide are used per part by weight of the fatty acid.

6. The preparation of claim 1 or 2 containing remaining water in an amount of 0.1 to 5% W/W per total weight of said preparation.

7. A fat emulsion obtainable by reconstituting the lyophilized preparation of claim 1 or 2 into emulsion form.

* * * * *